United States Patent
Folk et al.

(10) Patent No.: US 10,188,396 B2
(45) Date of Patent: Jan. 29, 2019

(54) APPARATUS AND METHOD FOR DELIVERING AN EMBOLIC COMPOSITION

(75) Inventors: Christopher Folk, Los Angeles, CA (US); David Franco, Costa Mesa, CA (US)

(73) Assignee: Covidien LP, Mansfield, MA (US)

( * ) Notice: Subject to any disclaimer, the term of this patent is extended or adjusted under 35 U.S.C. 154(b) by 1509 days.

(21) Appl. No.: 13/567,125

(22) Filed: Aug. 6, 2012

(65) Prior Publication Data
US 2014/0039459 A1 Feb. 6, 2014

(51) Int. Cl.
| A61B 17/12 | (2006.01) |
| A61M 25/00 | (2006.01) |
| A61M 25/10 | (2013.01) |
| A61B 17/00 | (2006.01) |
| A61B 17/22 | (2006.01) |

(52) U.S. Cl.
CPC .. *A61B 17/12031* (2013.01); *A61B 17/12113* (2013.01); *A61B 17/12186* (2013.01); *A61M 25/0075* (2013.01); *A61B 2017/00292* (2013.01); *A61B 2017/1205* (2013.01); *A61B 2017/22038* (2013.01); *A61M 2025/0018* (2013.01); *A61M 2025/0042* (2013.01); *A61M 2025/1052* (2013.01)

(58) Field of Classification Search
CPC ...... A61M 2039/0633; A61M 25/0075; A61M 2039/064; A61M 2025/0042; A61M 2025/0018; A61M 2025/1052; A61M 2039/0646
See application file for complete search history.

(56) References Cited

U.S. PATENT DOCUMENTS

| 5,085,635 A | 2/1992 | Cragg |
| 5,085,636 A | 2/1992 | Burns |
| 5,569,197 A | 10/1996 | Helmus et al. |
| 5,573,520 A | 11/1996 | Schwartz et al. |
| 5,792,118 A | 8/1998 | Kurth et al. |

(Continued)

FOREIGN PATENT DOCUMENTS

| JP | 2003508107 A | 3/2003 |
| JP | 2007319468 A | 12/2007 |

(Continued)

OTHER PUBLICATIONS

Notice of Preliminary Rejection, and translation thereof, from counterpart Korean Patent Application No. 10-2013-92439, dated Nov. 7, 2014, 10 pp.

(Continued)

*Primary Examiner* — Emily Schmidt
(74) *Attorney, Agent, or Firm* — Shumaker & Sieffert, P.A.

(57) ABSTRACT

A microcatheter for delivery of embolic fluids includes an outer member dimensioned for insertion within a blood vessel adjacent an embolization site. The outer member defines a first longitudinal lumen, and an inner member is selectively positionable within the first longitudinal lumen of the outer member. The inner member defines a second longitudinal lumen and has a delivery port in fluid communication with the second longitudinal lumen for passage and delivery of embolic fluids toward the embolization site. A valve is disposed within the outer member. The valve is dimensioned to establish a substantial seal about the inner member, to minimize entry of the embolic fluids within the first longitudinal lumen of the outer member subsequent to delivery thereof toward the embolization site.

19 Claims, 6 Drawing Sheets

(56) References Cited

U.S. PATENT DOCUMENTS

| | | | |
|---|---|---|---|
| 5,882,334 A * | 3/1999 | Sepetka et al. | 604/164.08 |
| 6,270,489 B1 | 8/2001 | Wise et al. | |
| 6,306,124 B1 * | 10/2001 | Jones et al. | 604/509 |
| 6,527,790 B2 | 3/2003 | Chien et al. | |
| 6,786,887 B2 | 9/2004 | Roychowdhury et al. | |
| 7,294,117 B2 | 11/2007 | Provost-Tine et al. | |
| 8,043,325 B2 | 10/2011 | Schrodt | |
| 2002/0072763 A1 | 6/2002 | Chien et al. | |
| 2004/0133222 A1 | 7/2004 | Tran et al. | |
| 2005/0065498 A1 | 3/2005 | McFerran | |
| 2005/0245963 A1 | 11/2005 | Kida et al. | |
| 2007/0213764 A1 | 9/2007 | Tran et al. | |
| 2008/0183183 A1 | 7/2008 | Kida et al. | |
| 2010/0198186 A1 | 8/2010 | Ackermann | |
| 2011/0118768 A1 | 5/2011 | Tran et al. | |
| 2011/0137399 A1 | 6/2011 | Chomas et al. | |
| 2011/0301571 A1 | 12/2011 | Guimaraes | |
| 2012/0116351 A1 | 5/2012 | Chomas et al. | |

FOREIGN PATENT DOCUMENTS

| | | |
|---|---|---|
| WO | WO 97/17998 A1 | 5/1997 |
| WO | 01015608 A1 | 3/2001 |
| WO | 0228465 A1 | 4/2002 |
| WO | WO 02/096264 A2 | 12/2002 |

OTHER PUBLICATIONS

Office Action, and translation thereof, from counterpart Russian Patent Application No. 2013134195/14, dated Oct. 19, 2014, 11 pp.

European Search Report for European Application No. 13177079.4, dated Nov. 28, 2013, 3 pages.

Notification of the First Office Action, and translation thereof, from counterpart Chinese Patent Application No. 201310337910.4, dated Dec. 10, 2014, 20 pp.

Notice of Preliminary Rejection, and translation thereof, from counterpart Korean Application No. 10-2015-0164014, dated Jan. 5, 2016, 9 pp.

Notice of Second Final Rejection, and translation thereof, counterpart Korean Application No. 10-2013-0092439, dated Oct. 21, 2015, 5 pp.

Notice of Final Rejection, and translation thereof, from counterpart Korean Patent Application No. 10-2013-0092439, dated Jun. 24, 2015, 5 pp.

Second Office Action, and translation thereof, from counterpart Chinese Application No. 201310337910.4, dated Jul. 21, 2015, 18 pp.

Examination Report from counterpart European Application No. 13177079.4-1501, dated Dec. 16, 2016, 4 pp.

Notice of Final Rejection, and translation thereof, from counterpart Korean Application No. 10-2015-0164014, dated Nov. 24, 2016, 5 pp.

Examination Report from counterpart European Application No. 13177079.4, dated Jun. 29, 2018, 5 pp.

Response to Examination Report dated Jun. 29, 2018, from counterpart European Application No. 13177079.4, filed Oct. 22, 2018, 14 pp.

Notification of Preliminary Rejection, and English translation thereof, from counterpart Korean Application No. 10-2016-0178933, dated Nov. 2, 2018, 10 pp.

* cited by examiner

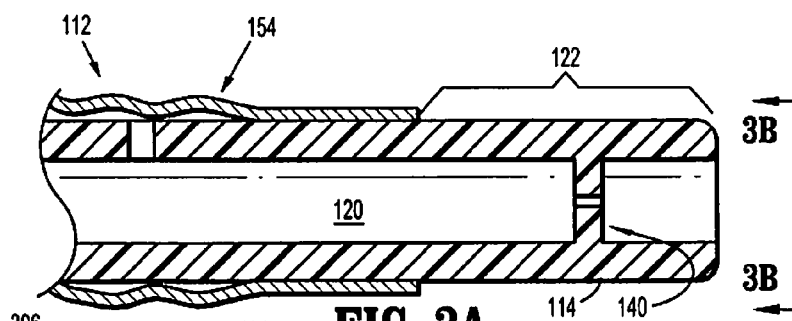
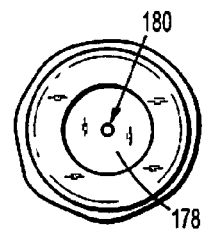
FIG. 3A    FIG. 3B
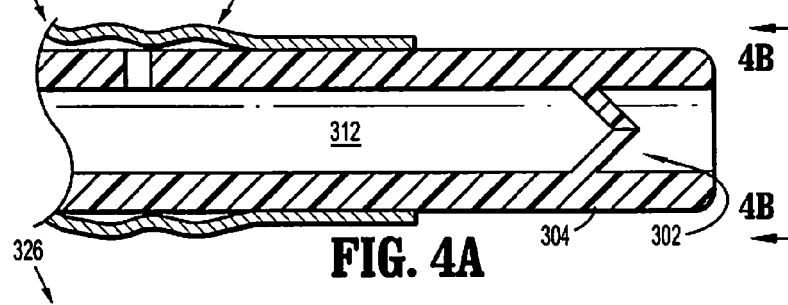
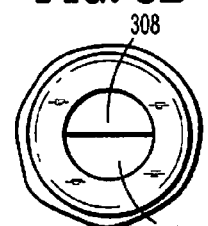
FIG. 4A    FIG. 4B
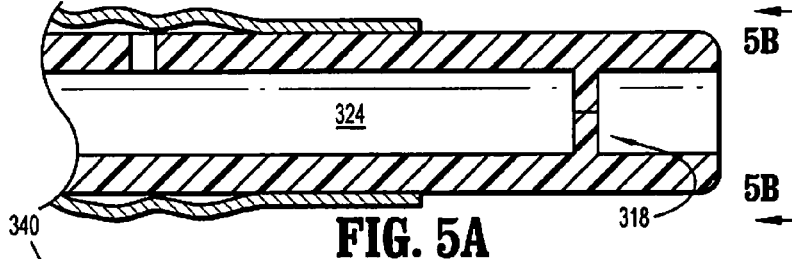
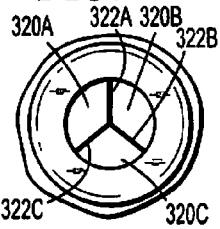
FIG. 5A    FIG. 5B
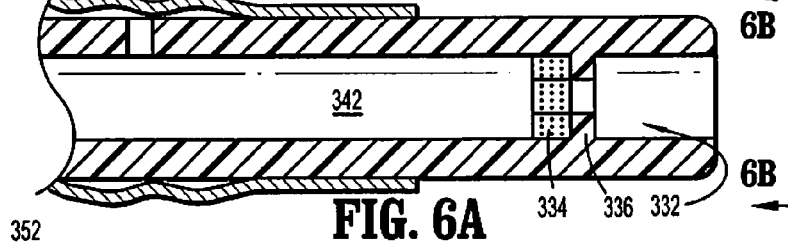
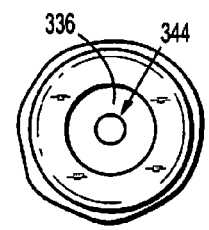
FIG. 6A    FIG. 6B
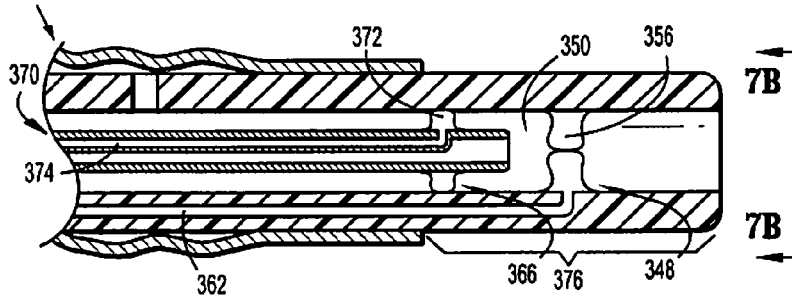
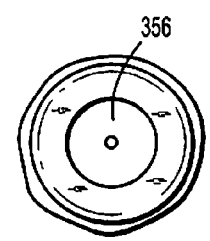
FIG. 7A    FIG. 7B

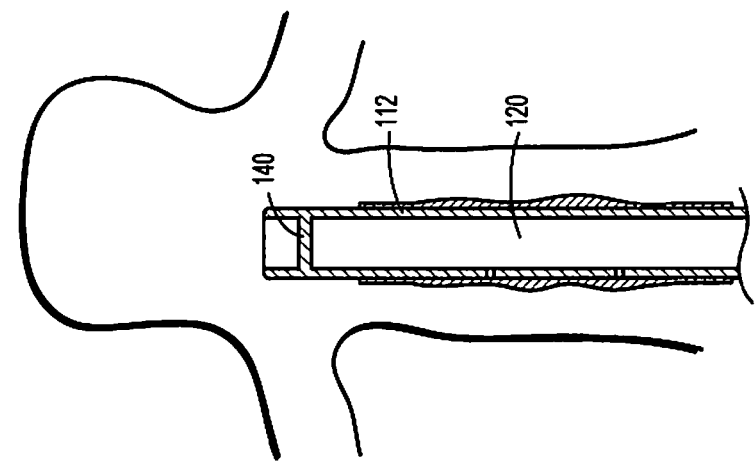
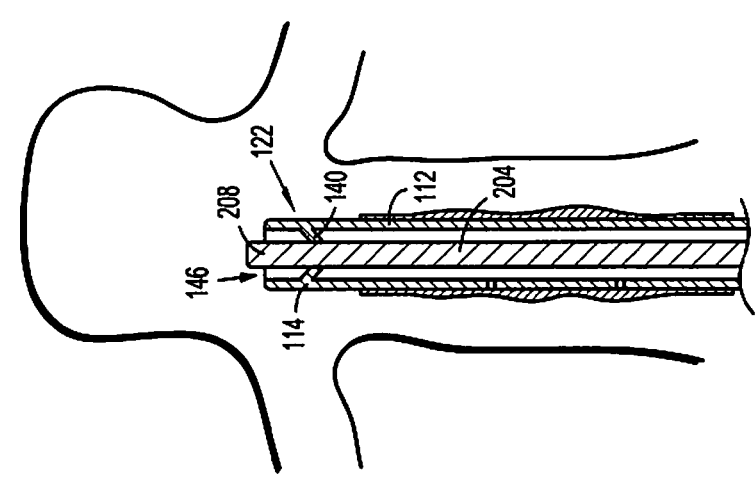
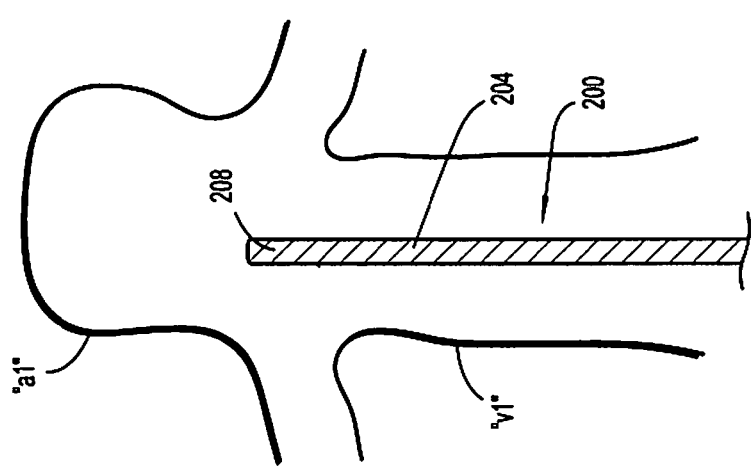

APPARATUS AND METHOD FOR DELIVERING AN EMBOLIC COMPOSITION

BACKGROUND

1. Technical Field

The present disclosure generally relates to intravascular devices and methods for facilitating delivery of an embolic composition into a blood vessel of a patient. In particular, the disclosure relates to an apparatus, system and method for the containment and restraint of a fluid embolic composition to or within an embolization site.

2. Description of Related Art

The delivery of fluid embolic compositions that solidify in vivo is particularly useful for a variety of reasons including treatment of blood vessels, tumors, aneurysms, arteriovenous malformations ("AVMs"), and arteriovenous fistulas ("AVF"). Delivery of such compositions is preferably accomplished via catheter techniques that permit the selective placement of the catheter at the delivery site. In practice, the catheter tip is directed to the vascular delivery site by use of conventional visualization techniques such as fluoroscopy, which allow the clinician to visualize the catheter tip. After placement of the catheter, the composition is introduced into the catheter and delivered to this site. Upon delivery, a biocompatible solvent of the composition dissipates into the blood, fluid, or tissue, and a water insoluble polymer of the composition precipitates to form a coherent mass, which solidifies in vivo. In the treatment of an AVM, for example, depending on the rate at which the liquid embolic composition is delivered and the amount of blood flow present, the dissipation of the biocompatible solvent may be sufficiently slow to permit the polymer, in liquid form, to migrate away from the AVM or embolization site. This migration may cause the occlusion of undesired locations in the vasculature, or the undesired occlusion of an intravascular device provided for delivering the liquid embolic composition.

Accordingly, it would be desirable to provide an apparatus for delivery of a liquid embolic composition to an AVM or aneurysm to prevent the embolic composition from passing outside of the desired embolization site into the vasculature.

Similarly, it would be desirable to provide an apparatus for delivery of a liquid embolic composition to an aneurysm that prevents backflow or reflux of the embolic composition into the vasculature.

SUMMARY

In accordance with one embodiment of the present disclosure, a microcatheter for delivery of embolic fluids includes an outer member dimensioned for insertion within a blood vessel adjacent an embolization site. The outer member defines a first longitudinal lumen, and an inner member is selectively positionable within the first longitudinal lumen of the outer member. The inner member defines a second longitudinal lumen and has a delivery port in fluid communication with the second longitudinal lumen for passage and delivery of embolic fluids toward the embolization site. A valve is disposed within the outer member. The valve is dimensioned to establish a substantial seal about the inner member, to thereby minimize entry of the embolic fluids within the first longitudinal lumen of the outer member subsequent to delivery of the fluids toward the embolization site.

The outer member may include an expandable member disposed on an exterior wall surface adjacent the delivery port. The expandable member may be dimensioned to expand and engage an interior wall portion of the blood vessel to at least partially isolate the embolization site. The expandable member may include an inflatable balloon. The inflatable balloon may be in fluid communication with the first longitudinal lumen of the outer member, and may be adapted to inflate upon passage of inflation fluids through the first longitudinal lumen.

The valve may be monolithically formed with the outer member, or the valve may be connected to an inner wall surface of the outer member. The valve may be dimensioned and adapted to substantially close in the absence of the inner member to substantially close the first longitudinal lumen of the outer member. The valve may comprise a passive valve, and the passive valve may comprise a plurality of resilient flaps formed by a plurality of radial slits. The plurality of resilient flaps may be biased to normally close the first longitudinal lumen when the inner member is removed from the passive valve. The passive valve may comprise an active hydrogel configured to harden in the presence of blood.

According to a further aspect of the disclosure, a system for embolizing a body lumen includes a microcatheter dimensioned for insertion within a blood vessel and being advanceable within the blood vessel to an embolization site. The microcatheter includes an outer member and an inner member selectively positionable within the outer member and defining a fluid lumen terminating at a fluid port. A valve is disposed within the outer member, and is adapted to establish a seal about the inner member when positioned within the outer member. The system further includes a fluid source having an embolic composition and being in fluid communication with the fluid lumen of the inner member. The embolic composition is deliverable to exit the fluid port for delivery within the embolization site.

The system may include a balloon member mounted about the outer member. The balloon member may be adapted for expansion to engage an interior wall of the blood vessel to at least partially isolate the embolization site to assist in containing the embolic composition within the embolization site. The system may further include a guidewire to facilitate accessing the embolization site. The guidewire may be dimensioned to be received within the outer member. The valve may be adapted to substantially close in the absence of the inner member.

According to a further aspect of the disclosure, a method of embolizing a body lumen includes the steps of: (i) advancing a guidewire through a vasculature to position a leading end of the guidewire at a target location; (ii) advancing an outer member over the guidewire until a leading end of the outer member is adjacent the leading end of the guidewire; (iii) withdrawing the guidewire from outer member; (iv) inserting an inner member through the outer member until a leading end of the inner member is disposed adjacent the leading end of the outer member; and (v) delivering an embolic composition to the target location through the inner member.

The step of advancing the guidewire may include positioning the leading end of the guidewire at a location within the vasculature that is distal of an aneurysm. The step of inserting an inner member through the outer member may include forming a seal between the outer and inner members. The method may further include the steps of: (vi) providing an inflatable balloon on an exterior wall surface of the outer member; and (vii) introducing an inflation fluid into the outer member to inflate the balloon.

BRIEF DESCRIPTION OF THE DRAWINGS

Embodiments of the present disclosure will be readily appreciated by reference to the drawings wherein:

FIGS. 3A-3B are enlarged, side cross-sectional and end views illustrating the passive valve of FIG. 2 within the outer member;

FIGS. 4A-6B are enlarged, side cross-sectional and end views illustrating alternate embodiments of passive valves in accordance with the principles of the present disclosure;

FIGS. 7A-7B are enlarged, side cross-sectional and end views illustrating active valves in accordance with the principles of the present disclosure;

FIGS. 8A-8F are partial, schematic views of the system of FIG. 1 in various stages of use at a first target location within the vasculature of a patient.

DESCRIPTION

Figure 1:
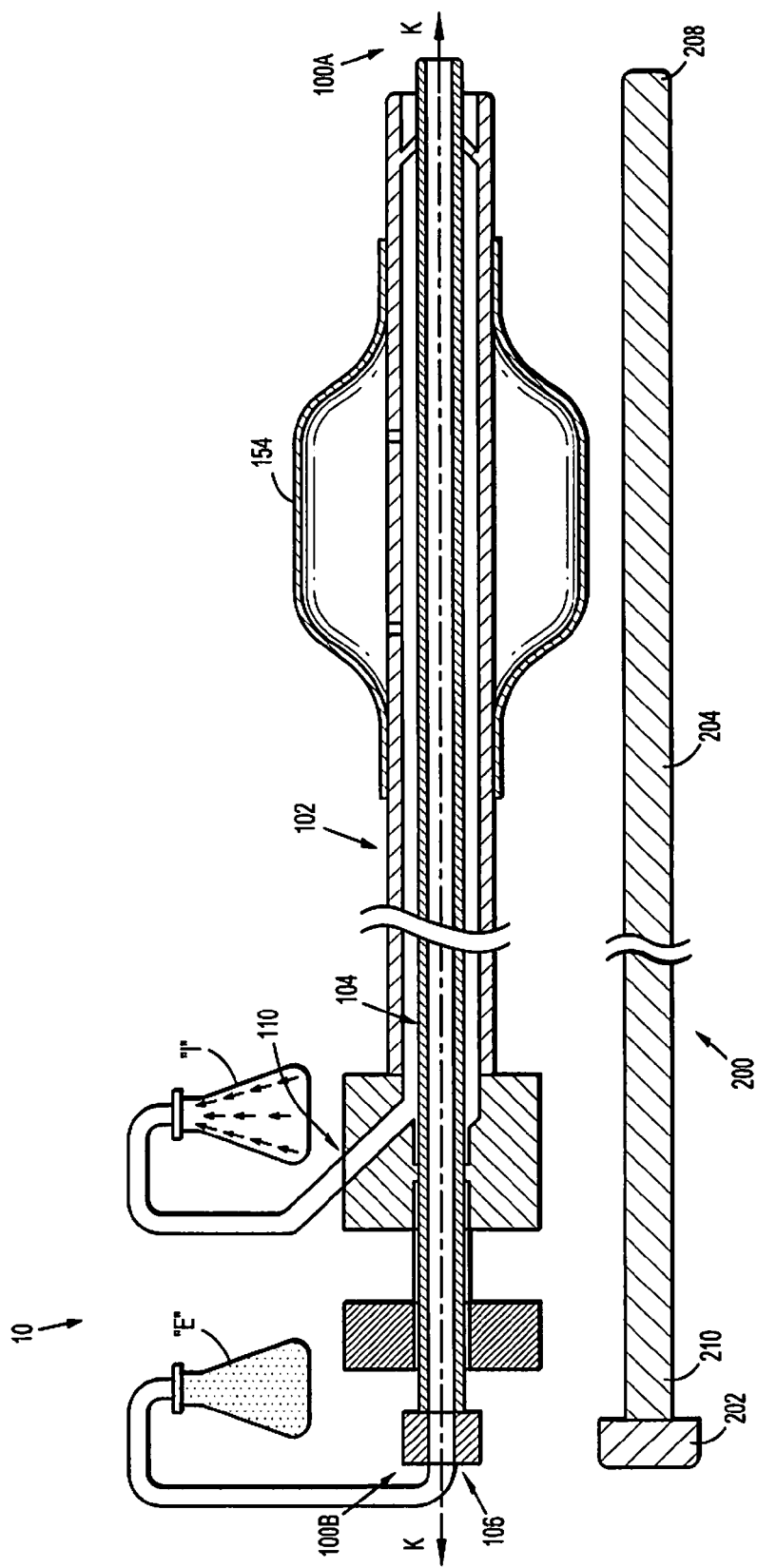
FIG. 1 is cross-sectional view of a medical system for delivering an embolic composition to a patient in accordance with the principles of the present disclosure, the system including an elongate microcatheter in fluid communication with an embolic composition and an inflation fluid, and a guidewire disposed outside the microcatheter.

In the following description, the terms "proximal" and "distal" as used herein refer to the relative position of the instrument in a lumen. The "proximal" or "trailing" end of the instrument is generally the segment of the instrument that extends outside the body of a patient and is closest to the clinician. The "distal" or "leading" end of the instrument is the segment of the instrument placed farthest into a body lumen from the entrance site.

The microcatheter of the present disclosure includes has particular application in an intracranial or neurovascular procedure. However, the microcatheter may be used in any interventional, diagnostic, and/or therapeutic procedure including coronary vascular, peripheral vascular, and gastrointestinal applications in addition to a neurovascular application. The microcatheter may be a component of an apparatus or system used in conjunction with any of the above applications. As discussed in greater detail hereinbelow, the apparatus or system may include additional components including, e.g., a guidewire, an embolic fluid source or any other component necessary to facilitate the performance of the contemplated medical procedure.

In the figures below, the full length of the microcatheter and/or guidewire is not shown. The length of the microcatheter and/or guidewire can vary depending on the type of interventional procedure, though typically it ranges in length from 30 to 400 centimeters (cm). Common lengths of microcatheters and/or guidewires for coronary, peripheral and neurovascular interventions may range from 170 to 300 cm.

The various embodiments of the disclosure will now be described in connection with the drawing figures. It should be understood that for purposes of better describing the disclosure, the drawings may not be to scale. Further, some of the figures include enlarged or distorted portions for the purpose of showing features that would not otherwise be apparent.

Referring to FIG. 1, a medical system 10 of the present disclosure may include an elongate microcatheter 100, a source of a fluid embolic composition "E" and a source of an inflation media or fluid "I." The medical system 10 may further include a guidewire 200 upon which microcatheter 100 may be positioned or advanced toward a targeted treatment site. The microcatheter 100 defines a longitudinal axis K-K, and has a leading end 100A and a trailing end 100B. The microcatheter 100 includes an outer catheter member 102 and an inner catheter member 104 disposed therein. The inner catheter member 104 is movable within the outer catheter member 102, and as discussed below, may be removed from the outer catheter member 102 to permit at least partial passage of the guidewire 200 through the outer catheter member 102.

In general, the guidewire 200 includes an actuator 202 and an elongate guide member 204 extending from the actuator 202. The elongate guide member 204 is dimensioned for insertion within the vasculature or a blood vessel of a subject, and includes a leading end 208 and a trailing end 210. The guidewire 200 may include any commonly used guidewire.

The source of embolic composition "E" is provided in fluid communication with a proximal access port 106 of the inner catheter member 104. The embolic composition "E" may be any biocompatible composition that solidifies within the body such as a biocompatible polymer dissolved in a biocompatible solvent, e.g., dimethylsulfoxide (DMSO), acetone and the like. Examples of embolic compositions are described in U.S. Pat. Nos. 5,667,767, 5,580,568 and 5,695,480, the entire disclosure of each being incorporated by reference herein. The source of the embolic composition "E" may include a syringe, pump or other mechanism (not shown) to permit a clinician to selectively control the flow of the embolic composition "E" to and through the inner catheter member 104.

The source of inflation fluid "I" is provided in fluid communication with a first proximal access port 110 of the outer catheter member 102. The inflation fluid "I" may include fluids such as air or saline, and may be selectively transmitted to the outer catheter member 102 to inflate an inflatable balloon 154 thereof.

Figure 2:
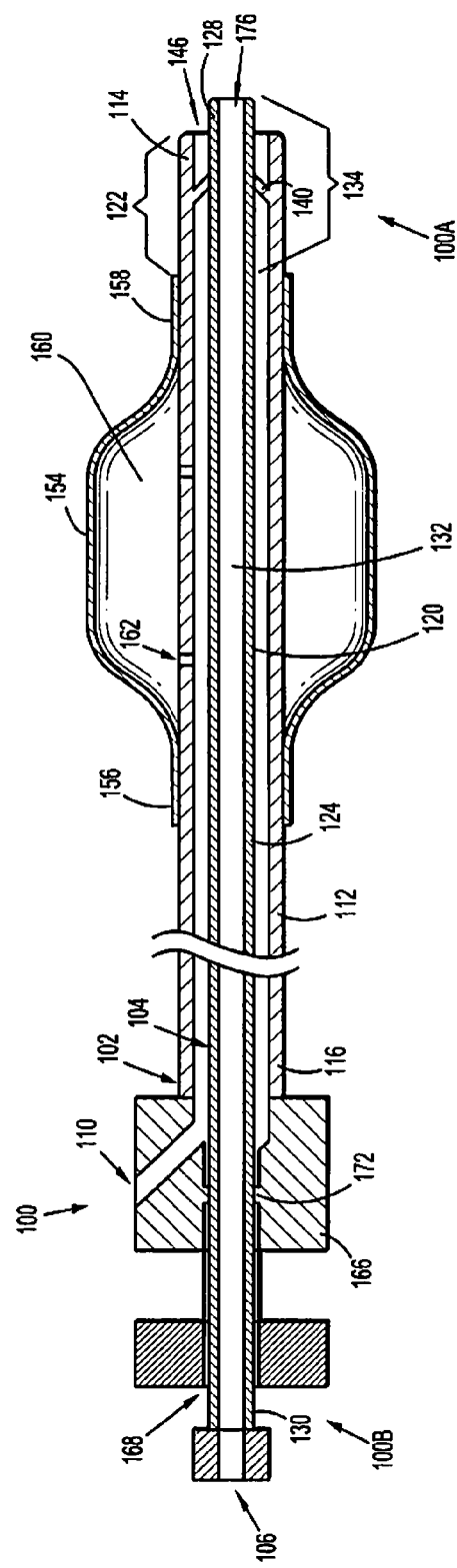
FIG. 2 is a cross-sectional view of the microcatheter of FIG. 1 illustrating an outer member, an inner catheter member disposed within a lumen of the outer member, and a passive valve disposed within the outer member.

Referring now to FIG. 2, in conjunction with FIG. 1, further features of microcatheter 100 are illustrated and will be discussed in greater detail. The outer catheter member 102 of the microcatheter 100 generally includes an outer elongate member 112 which is dimensioned for insertion within a blood vessel adjacent an embolization site. The outer elongate member 112 has a leading end 114, a trailing end 116, and at least one longitudinal lumen 120 extending therethrough. The outer elongate member 112 may be constructed of a flexible material, e.g., a cylindrical stock of one or more polymers, such as Grilamid brand polyamide/nylon from EMS Chemie, Switzerland, Pebax brand polyether/polyamide, from Actinofina Chemicals, France and the like. A first leading-end segment 122 is defined at the leading end 114 of the outer elongate member 112.

The inner catheter member 104 generally includes an inner elongate member 124, which is selectively positionable within the longitudinal lumen 120 of the outer elongate member 112. The inner elongate member 124 may be constructed of materials similar to the outer elongate member 112 discussed above, and may have an outer diameter substantially similar to the elongate guide member 204 of the guidewire 200 (FIG. 1). The inner elongate member 124 has a leading end 128, a trailing end 130, and at least one longitudinal lumen 132 extending therethrough. The longitudinal lumen 132 defines a fluid lumen and may extend the entire length of the inner elongate member 124. A second leading-end segment 134 is defined at the leading end 128 of the inner elongate member 124.

The first leading-end segment 122 adjacent the leading end 114 of the outer elongate member 112 may be monolithically formed with the outer elongate member 112, or may be a separate component attached to the outer elongate member 112 through bonding, adhesive, thermofusion techniques or other known methods. The first leading-end segment 122 includes a distal access port 146 at the distal end of lumen 120.

A valve 140 is disposed within the first leading-end segment 122 or the outer elongate member 112. The valve 140 is dimensioned to establish a substantial seal about the inner elongate member 124, to thereby minimize entry of embolic fluids within the longitudinal lumen 120 of the outer elongate member 112 subsequent to delivery of the embolic fluids toward the embolization site. The valve 140 is configured to selectively close an annular gap between the outer and inner elongate members 112, 124.

The inflatable balloon 154 is an expandable member supported near the leading end 114 of the outer elongate member 112. The balloon 154 is connected to an exterior wall surface of the outer elongate member 112 at a proximal seal area 156 and a distal seal area 158, thereby defining an enclosed interior space 160. The enclosed interior space 160 is in fluid communication with the lumen 120 through inflation holes 162 extending laterally through the outer elongate member 112. As discussed in greater detail hereinbelow, the balloon 154 is dimensioned to expand and engage an interior wall portion of a blood vessel to at least partially isolate an embolization site.

The outer catheter member 102 may further include a manifold 166 at the trailing end 116 of the outer elongate member 112. The manifold 166 includes the first proximal access port 110 and a second proximal access port 168. The first proximal access port 110 is configured for connection to the source of inflation fluid "I." The inflation fluid "I" may be selectively transmitted into the second proximal access port 110, and then through the lumen 120 of the outer elongate member 112 and the inflation holes 162 to the interior space 160 to inflate the balloon 154. The second proximal access port 168 receives the inner catheter member 104. A sealing member 172 is provided within the manifold 166 between the first and second proximal access ports 110, 168. The sealing member 172 may be constructed of a flexible, elastomeric material and permits fluid isolation of the first and second proximal access ports 110, 168.

The inner catheter member 104 includes a hub or access port 106 at the trailing end 130 of the inner elongate member 124. The access port 106 is in fluid communication with the longitudinal lumen 132. At the leading end 128 of the inner elongate member 124, the second leading-end segment 134 is defined, which includes a distal access port 176 at a distal end of the longitudinal lumen 132. The distal access port 176 defines a fluid port or delivery port in fluid communication with the longitudinal lumen 132 for passage and delivery of embolic fluids toward an embolization site. The embolic composition "E" (FIG. 1) may be selectively delivered to the microcatheter 100 through the proximal access port 106 of the inner catheter member 104. The embolic composition "E" may be selectively transmitted through the longitudinal lumen 132 of the inner catheter member 104 to the second leading-end segment 134, and may be expelled through the distal access port 176.

The inner elongate member 124 is selectively positionable within the lumen 120 of the outer elongate member 112, and is longitudinally movable therewithin. The inner elongate member 124 engages the valve 140 whereby the valve establishes a sealing relationship with the inner elongate member 124. A mechanism (not shown) may be provided to releasably secure or lock the inner elongate member 124 to the outer elongate member 112. Alternatively, the sealing member 172 and/or the valve 140 may establish a frictional relationship with the inner elongate member 124 to impede longitudinal movement of the inner elongate member 124.

Referring now to FIGS. 3A and 3B, the leading end 114 of the outer elongate member 112 is depicted with the balloon 154 in a deflated configuration. The valve 140 comprises a membrane 178, which may be formed monolithically with, or attached to, an outer wall of the first leading-end segment 122. A central aperture 180 extends through the membrane 178. The aperture 180 may have a diameter of about 0.005 inches, and, thus, the lumen 120 may be substantially, but not be completely closed by the valve 140. The membrane 178 may be constructed of a material having sufficient resilience to permit elastic expansion of the aperture 180 to facilitate passage of the inner elongate member 124 (FIG. 2) and/or the elongate guide member 204 of the guidewire 200 (FIG. 1) therethrough while also creating a substantial sealing relation about the outer surfaces of these components. Suitable materials for the valve 140 include thermoplastic elastomers, e.g., polyisoprene, or natural rubber. In an alternative, the valve 140 may be fabricated from a low durometer thermoplastic elastomer or a gel material. Other materials are also envisioned. The valve 140 may be characterized as a passive valve since the valve 140 responds to the introduction of the guidewire 200 (FIG. 1) or the inner elongate member 124 therethrough by automatically forming a seal therewith without any further positive action by a clinician.

Alternate embodiments of valves in accordance with the present disclosure are illustrated in FIGS. 4A through 7B. A duckbill valve 302 is depicted in FIGS. 4A and 4B at a leading end 304 of an outer elongate member 306. The valve 302 is configured generally as a conical or tapered duckbill including first and second leaflets 308, 310. The leaflets 308, 310 are resilient and biased to the closed configuration in which an inner lumen 312 of the elongate member 306 is completely closed. The leaflets 308, 310 are inclined to depend radially inwardly in the distal direction. The distal incline allows the leaflets 308, 310 to readily open to permit a sealed passage of the inner elongate member 124 (FIG. 2) from a proximal direction, and also to resist the influx of a fluid such as blood and/or an embolic composition "E" at a relatively higher pressure into the inner lumen 312 from the distal side of the valve 302. In other embodiments, a duckbill valve (not depicted) may be provided that exhibits a proximal incline to resist opening when a relatively higher pressure inflation fluid "I" (FIG. 1) is introduced into the inner lumen 312 to inflate balloon 154.

A tri-leaf valve 318 is depicted in FIGS. 5A and 5B. The tri-leaf valve 318 is constructed of a plurality of resilient flaps 320A, 320B, 320C formed by a plurality of radial slits 322A, 322B, 322C. Any number of flaps and slits may be provided that cooperate to permit the passage of the guidewire 200 (FIG. 1) or the inner elongate member 124 (FIG. 2) and resiliently return to a relatively closed configuration (as illustrated) upon removal of the guidewire 200 or the inner elongate member 124. The flaps 320A, 320B, 320C may be constructed of a resilient material to provide a bias to return the flaps 320A, 320B, 320C to the closed configuration in which a lumen 324 through an outer elongate member 326 is closed.

Referring now to FIGS. 6A and 6B, a valve 332 includes a self-sealing or closing plug or membrane 334 positioned proximally with respect to a flexible membrane 336. The flexible membrane 336 may be similar to the membrane 178 (FIG. 3B) described above, and the self-sealing membrane 336 may be constructed of an active hydrogel. The membrane 336 may provide a seal with a guidewire 200 (FIG. 1) as outer elongate member 340 is moved along the guidewire 200 to position the outer elongate member 336 within a vasculature. Thereafter, the guidewire 200 may be withdrawn through lumen 342 permitting blood to move through an aperture 344 in the membrane 336 to contact the membrane 334. In the presence of blood, the membrane 334 may swell to occupy an entire inner diameter of the lumen 342.

Each of the valves 140, 302, 318 and 332 described above may be characterized as passive since each is configured to automatically form a seal with an object inserted therethrough without any further positive action by a clinician. In other embodiments, an active valve, such as valve 348 as depicted in FIGS. 7A and 7B, may be employed to selectively close a lumen 350 extending through an outer elongate member 352. The valve 348 includes an inflatable balloon 356 disposed on an interior side of the outer elongate member 352. The balloon 356 is in fluid communication with an inflation lumen 362 that extends to a proximal end (not shown) of the outer elongate member 352. A clinician may selectively deliver the inflation fluid "I" through the lumen 362 to selectively expand the balloon 356, and thereby substantially close the lumen 362.

With reference to FIG. 7A, a valve 366 may also be provided on an inner elongate member 370 to permit selective closure of the annular gap between outer and inner elongate members 352, 370. The valve 366 may include an inflatable balloon 372 in fluid communication with an inflation lumen 374. The balloon 372 is disposed on an exterior of the inner elongate member 370 such that the balloon 372 may be inflated to selectively obstruct the lumen 350 when positioned within a leading-end segment 376 of outer elongate member 352 by a clinician.

Figure 8D:
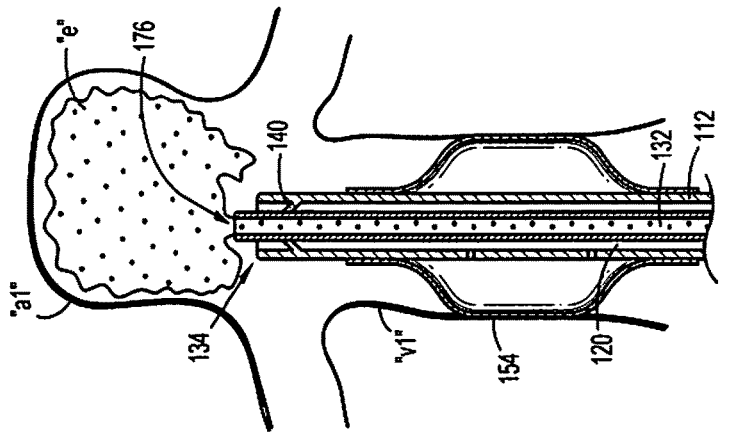

Referring now to FIGS. 8A through 8F, a procedure for treating an aneurysm "a1" with the system 10 (FIG. 1) is discussed. Initially, the elongate guide member 204 of guidewire 200 may be positioned within the vasculature of a patient (FIG. 8A). The elongate guide member 204 may be advanced through a vessel "v1" to position the leading end 208 of the elongate guide member 204 at a target location with respect to the aneurysm "a1" as determined by the clinician. Next, the outer elongate member 112 may be advanced over the elongate guide member 204 until the distal access port 146 and the first leading-end segment 122 are positioned adjacent the leading end 208 of the elongate guide member 204 (FIG. 8B). The leading end 114 of the outer elongate member 112 is thus positioned at the target location, e.g., adjacent the aneurysm "a1." The valve 140 may establish a sealing relation with the elongate guide member 204 preventing the influx of blood into the outer elongate member 112 through the distal access port 146.

The elongate guide member 204 may then be withdrawn from the longitudinal lumen 120 leaving the outer elongate member 112 in place (FIG. 8C). The valve 140 may substantially close the lumen 120 in the absence of the elongate guide member 204. Thus, the inflation holes 162 may be protected from an influx of blood or other fluids, which may otherwise clog the inflation holes 162.

Figure 8E:
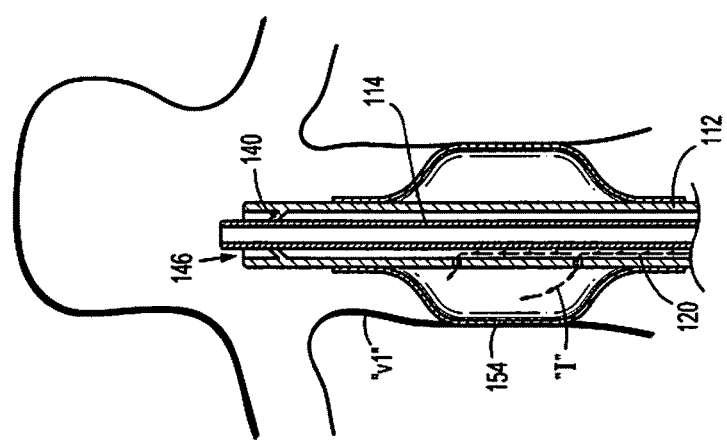
Figure 8F:
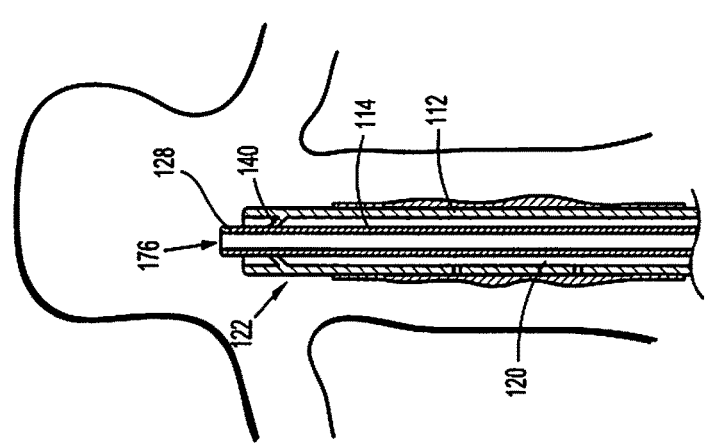

With the outer elongate member 112 positioned within the vasculature, the inner elongate member 114 may be inserted through the longitudinal lumen 120 of the outer elongate member 112 until the distal access port 176 at the leading end 128 of the inner elongate member 114 is positioned distally of the valve 140 (FIG. 8D). The valve 140 establishes a sealing relationship with the inner elongate member 114. With a seal established between the valve 140 and the inner elongate member 114, the inflation fluid "I" may be introduced and transmitted through the longitudinal lumen 120 of the outer elongate member 112 to inflate the balloon 154 (FIG. 8E). The balloon 154 expands to engage interior wall portions of vessel "v1" and may form a seal therewith to at least partially isolate an embolization site. The valve 140 prevents the escape of the inflation fluid "I" through the distal access port 146 of the longitudinal lumen 120. With the balloon 154 expanded, the embolic composition "E" may be transmitted through the lumen 132 of the inner elongate member 124 and expelled through the distal access port 176 of second leading-end segment 134 (FIG. 8F).

The flow of embolic composition "E" may be continued until the aneurysm "a1" or the desired embolization site is filled and the embolic composition "E" solidifies. During the procedure, backflow of the embolic composition "E" through the vessel "v1" is prevented by the balloon 154, and backflow of the embolic composition "E" through the longitudinal lumen 120 of the outer elongate member 112 is prevented by the valve 140.

Figure 9A:
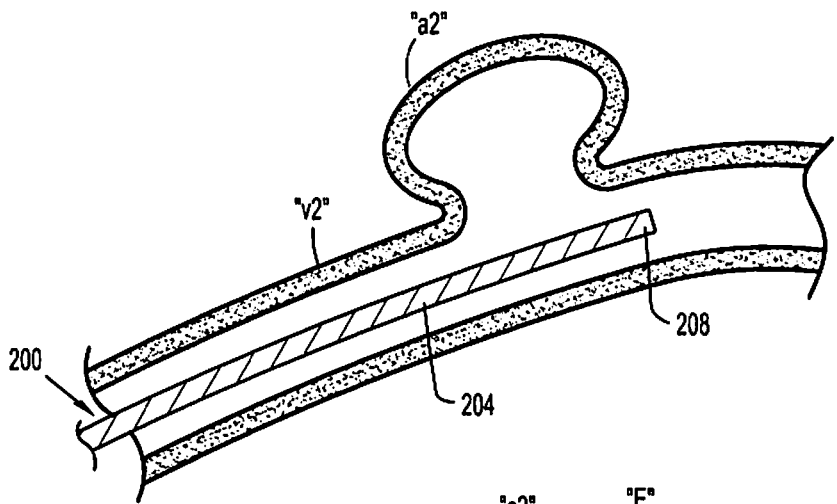
FIGS. 9A-9C are partial, schematic views of the system of FIG. 1 in various stages of an alternate use at a second target location within the vasculature of the patient.
Figure 9B:
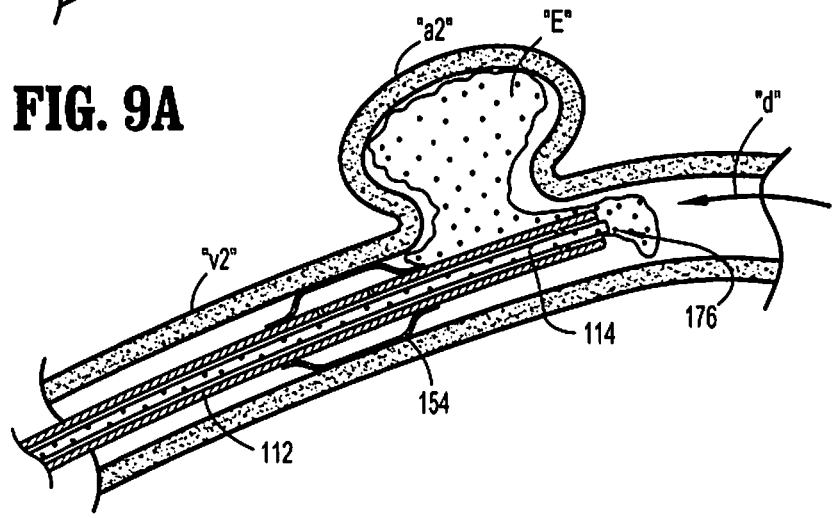
Figure 9C:
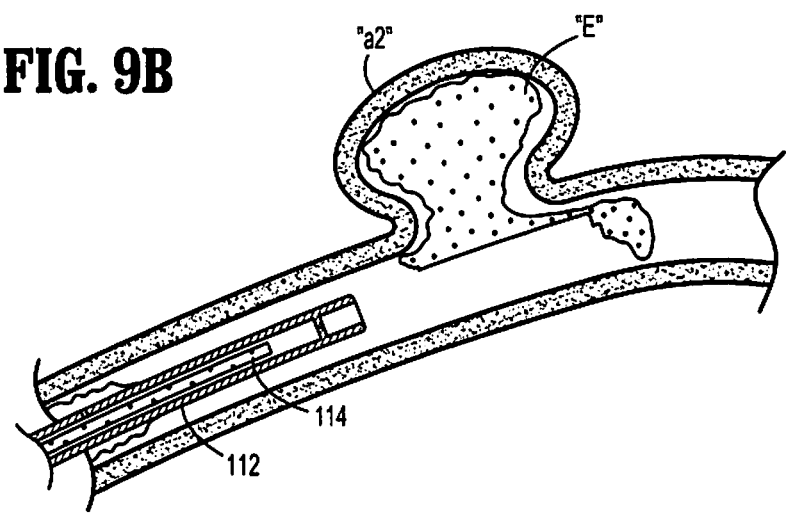

Referring now to FIGS. 9A through 9C, an alternate procedure is described for treating an aneurysm "a2" with the system 10 (FIG. 1). Initially, the elongate guide member 204 of guidewire 200 is positioned within the vasculature "v2" of a patient such that the leading end 208 of the elongate guide member 204 is advanced until positioned distal of the aneurysm "a2" (FIG. 9A). Thereafter, the outer elongate member 112 may be advanced over the elongate guide member 204 toward the aneurysm"a2", the elongate guide member 204 may be withdrawn from the longitudinal lumen 120 of the outer elongate member 112 and the inner elongate member 114 may be inserted through the outer elongate member 112. The balloon 154 may be inflated, and the embolic composition "E" may be delivered through the inner elongate member 114 as described above (FIG. 9B).

Since the leading end 208 of the elongate guide member 204 is positioned distal of the aneurysm "a2," the distal access port 176 from which the embolic composition "E" is expelled may also be positioned distal of the aneurysm "a2." The embolic composition "E" may be induced to flow in a proximal or trailing direction relative to the inserted microcatheter 100 into the aneurysm "a2" by the flow of blood in the direction "d" within the vasculature "v2." The proximal flow of the embolic composition "E" may cause the embolic composition "E" to solidify within the aneurysm "a2" and against exterior surfaces of the outer and inner elongate members 112, 114.

When the embolic composition "E" is solidified, the inner elongate member 114 may be withdrawn from the outer elongate member 112 and the outer elongate member 112 may be withdrawn from the aneurysm "a2" (FIG. 9C). The embolic composition "E" may have a self-adherent quality such that the embolic composition maintains a coherent structure when the elongate members 112, 114 are disconnected from the embolic composition "E." The embolic composition "E" will thus remain at the aneurysm "a2," and portions of the embolic composition "E" will not break off and migrate to undesired locations within the vasculature "v2."

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A microcatheter for delivery of embolic fluids, which comprises:
   an outer member dimensioned for insertion within a blood vessel adjacent an embolization site, the outer member defining a first longitudinal lumen;
   an inner member selectively positionable within the first longitudinal lumen of the outer member, the inner member defining a second longitudinal lumen and having a delivery port in fluid communication with the second longitudinal lumen for passage and delivery of embolic fluids toward the embolization site; and
   a valve disposed within the outer member, the valve dimensioned to establish a substantial seal about the inner member, to minimize entry of the embolic fluids within the first longitudinal lumen of the outer member subsequent to delivery thereof toward the embolization site,
   wherein the outer member includes an expandable member disposed on an exterior wall surface thereof adjacent the delivery port, the expandable member dimensioned to expand and engage an interior wall portion of the blood vessel to at least partially isolate the embolization site.

2. The microcatheter according to claim 1, wherein the expandable member includes an inflatable balloon.

3. The microcatheter according to claim 2, wherein the inflatable balloon is in fluid communication with the first longitudinal lumen of the outer member, and is adapted to inflate upon passage of inflation fluids through the first longitudinal lumen.

4. The microcatheter according to claim 1, wherein the valve is monolithically formed with the outer member.

5. The microcatheter according to claim 1 wherein the valve is connected to an inner wall surface of the outer member.

6. The microcatheter according to claim 1, wherein the valve is dimensioned and adapted to substantially close in the absence of the inner member to substantially close the first longitudinal lumen of the outer member.

7. The microcatheter according to claim 1, wherein the valve comprises a passive valve.

8. The microcatheter according to claim 7, wherein the passive valve comprises a plurality of resilient flaps formed by a plurality of radial slits.

9. The microcatheter according to claim 8, wherein the plurality of resilient flaps are biased to normally close the first longitudinal lumen when the inner member is removed from the passive valve.

10. The microcatheter according to claim 7, wherein the passive valve comprises an active hydrogel configured to harden in the presence of blood.

11. A system for embolizing a body lumen, which comprises:
   a microcatheter dimensioned for insertion within a blood vessel and being advanceable within the blood vessel to an embolization site, including:
      an outer member;
      an inner member selectively positionable within the outer member and defining a fluid lumen terminating at a fluid port;
      a valve disposed within the outer member, and adapted to establish a seal about the inner member when positioned within the outer member; and
   a fluid source including an embolic composition in fluid communication with the fluid lumen of the inner member, and deliverable to exit the fluid port for delivery within the embolization site,
   wherein the outer member includes an expandable member disposed on an exterior wall surface thereof adjacent the fluid port, the expandable member dimensioned to expand and engage an interior wall portion of the blood vessel to at least partially isolate the embolization site.

12. The system according to claim 11, wherein the expandable member includes a balloon member mounted about the outer member.

13. The system according to claim 11 further including a guidewire to facilitate accessing the embolization site.

14. The system according to claim 13 wherein the guidewire is dimensioned to be received within the outer member.

15. The system according to claim 11 wherein the valve is adapted to substantially close in the absence of the inner member.

16. A method of embolizing a body lumen, the method comprising:
   advancing a guidewire through a blood vessel to position a leading end of the guidewire adjacent an embolization site;
   advancing an outer member over the guidewire and within the blood vessel until a leading end of the outer member is disposed adjacent the leading end of the guidewire and adjacent the embolization site, the outer member defining a first longitudinal lumen;
   withdrawing the guidewire from the outer member;
   inserting an inner member within the first longitudinal lumen of the outer member until a leading end of the inner member is disposed adjacent the leading end of the outer member, the inner member defining a second longitudinal lumen and having a delivery port in fluid communication with the second longitudinal lumen for passage and delivery of embolic fluids toward the embolization site; and
   delivering the embolic fluids through the second longitudinal lumen to the embolization site,
   wherein a valve is disposed within the outer member, the valve dimensioned to establish a substantial seal about the inner member, to minimize entry of the embolic fluids within the first longitudinal lumen of the outer member subsequent to delivery thereof toward the embolization site, and
   wherein the outer member includes an expandable member disposed on an exterior wall surface thereof adjacent the delivery port, the expandable member dimensioned to expand and engage an interior wall portion of the blood vessel to at least partially isolate the embolization site.

17. The method according to claim 16, wherein advancing the guidewire includes positioning the leading end of the guidewire at a location within the blood vessel that is distal of an aneurysm.

18. The method according to claim 16, wherein inserting an inner member within the first longitudinal lumen of the outer member includes forming a seal between the outer and inner members with the valve.

19. The method according to claim 16, further comprising:
   introducing an inflation fluid into the outer member to inflate the expandable member, wherein the expandable member includes an inflatable balloon.

* * * * *